United States Patent [19]
Dyer et al.

[11] Patent Number: 6,018,043
[45] Date of Patent: Jan. 25, 2000

[54] PROCESS FOR PREPARING GALANTHAMINE DERIVATIVES BY ASYMMETRIC REDUCTION

[75] Inventors: Ulrich Conrad Dyer; Jane Marie Paul; Raymond McCague, all of Cambridge, United Kingdom

[73] Assignee: Janssen Pharmaceutica, N.V., Belgium

[21] Appl. No.: 08/930,211

[22] PCT Filed: Apr. 4, 1996

[86] PCT No.: PCT/GB96/00843

§ 371 Date: Feb. 2, 1998

§ 102(e) Date: Feb. 2, 1998

[87] PCT Pub. No.: WO96/31453

PCT Pub. Date: Oct. 10, 1996

[30] Foreign Application Priority Data

Apr. 6, 1995 [GB] United Kingdom .................. 9507100
Jan. 22, 1996 [GB] United Kingdom .................. 9601227

[51] Int. Cl.$^7$ .................................................. C07D 487/00
[52] U.S. Cl. ........................................... 540/520; 540/521
[58] Field of Search ..................................... 540/520, 521

[56] References Cited

PUBLICATIONS

Szewczyk et al., "An Improved Synthesis of Galanthamine", J. Het. Chem., vol. 25(6), pp. 1809–1811, Nov. 1988.
Shieh et al., J. Org. Chem., "Asymmetric Transformation . . . ", vol. 59(18), pp. 5463–5465, Sep. 9, 1994.

Primary Examiner—Mukund J. Shah
Assistant Examiner—Tamthom N. Truong
Attorney, Agent, or Firm—Saliwanchik, Lloyd & Saliwanchik

[57] ABSTRACT

The subject invention concerns a process for preparing a compound of formula (3)

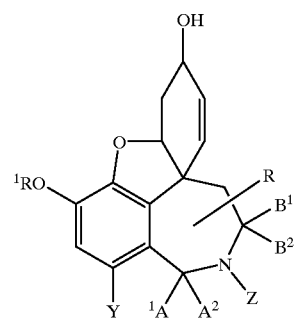

(3)

in enantio-enriched form, comprising reducing a compound of formula (4)

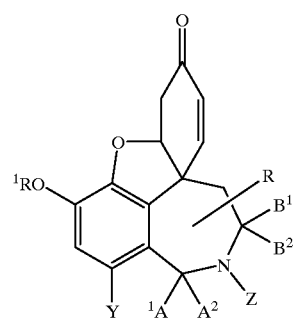

(4)

using an asymmetric enantiospecific reductant, wherein $A^1=A^2=H$ or $A^1, A^2=O$; $B^1=B^2=H$ or $B^1, B^2=O$; $Z=H$, $C_{1-20}$ alkyl or a precursor thereof, or a removable protecting group for nitrogen, e.g, acyl or alkyloxycarbonyl; $Y=H$ or a substituent; $R^1=C_{1-20}$ alkyl; and R is an optional, additional substituent.

7 Claims, No Drawings

PROCESS FOR PREPARING GALANTHAMINE DERIVATIVES BY ASYMMETRIC REDUCTION

FIELD OF THE INVENTION

This invention relates to a process for the production of enantio-enriched galanthamine, and derivatives thereof, by way of an asymmetric reduction reaction.

BACKGROUND TO INVENTION (−)-Galanthamine, and derivatives thereof, are useful for the treatment of Alzheimer's disease and related illnesses. Currently galanthamine is obtained by extraction from natural sources, such as daffodils or snowdrops. The yields of these extractive procedures are low, resulting in high costs and limited supplies of naturally-obtained galanthamine.

It is known that single enantiomer galanthamine (3) can be prepared from racemic narwedine (4) through resolution followed by reduction of the enone function, as depicted in Scheme 1 below. Usefully, since the enantiomers of narwedine (3) readily equilibrate (racemize) by way of reversible ring opening to a dienone, coupled to the fact that crystals of racemic (4) exist as a conglomerate of enantiomers, a dynamic resolution of (4) can be carried out by crystallisation with entrainment by crystals of the desired isomer; see Barton and Kirby, J. Chem. Soc. (C) (1962) p.806. However, in respect of a total synthesis, this route suffers the disadvantage that racemic narwedine itself is not readily available.

Barton described the use of lithium aluminium hydride to effect the above reduction, however significant amounts of epigalanthamine were also produced, which is undesirable. Reduction of narwedine using the Meerwein-Ponndorf-Verley conditions gave exclusively epigalanthamine. Subsequently it was disclosed in U.S. Pat. No. 5,428,159 that the requisite transformation could readily be achieved using L-Selectride; see Brown and Krishnamurthy, JACS (1972) p.7159. However, this reagent is expensive and only available in pilot plant quantities, and is therefore unsuitable for large scale production; see Rittmeyer, Chimica Oggi (1995) p.51. Alternative reagents disclosed in the prior art are either as esoteric as L-Selectride, or do not afford sufficiently high levels of diastereoselection.

SUMMARY OF THE INVENTION

According to a first aspect of the present invention, a process for preparing a compound of formula (3) in enantio-enriched form comprises reducing a compound of formula (4), both formulae being shown below, using an asymmetric reductant, and wherein $A^1=A^2=H$ or $A^1$, $A^2=O$; $B^1=B^2=H$ or $B^1$, $B^2=O$; $Z=H$, $C_{1-20}$ alkyl or a precursor thereof, or a removable protecting group for nitrogen, e.g. acyl or alkyloxycarbonyl; $Y=H$ or a substituent; $R^1=C_{1-20}$ alkyl; and R is an optional, additional substituent. Also, a further substituent can optionally be included in the aromatic ring.

The process of the invention is capable of preparing enantio-enriched galanthamine, or a derivative thereof, from either racemic or enantio-enriched narwedine, in greater enantiomeric excess than achieved by prior art processes.

According to a second aspect of the present invention, novel compounds have the general formula (3) in substantially single enantiomer form, wherein $A^1=A^2=B^1=B^2=H$, $R^1=Me$, and the other substituents are as defined above.

According to a third aspect of the present invention, bromogalanthamine is provided in substantially single enantiomer form.

Preferably, the above-described compounds have a configuration corresponding to (−)-galanthamine, allowing ready conversion to (−)-galanthamine.

DESCRIPTION OF THE INVENTION

The process of the present invention has two embodiments. A first embodiment proceeds via a kinetic resolution on reduction of a racemic enone precursor to the target compound, as outlined in Scheme 2, below. Through the use of an asymmetric reductant, only one enantiomer (A) of the enone is reduced into the corresponding galanthamine derivative, while the other enantiomer (B) is largely unreacted.

In a preferred case, any starting material that is not reduced by the asymmetric reductant can be recycled through racemisation with a base, and then subjected to the reduction/resolution process again. This means that, eventually, all starting material can be converted into the desired enantiomer of the target compound. Ideally, the reaction can be performed as a dynamic resolution in which equilibration between the two enantiomers takes place rapidly during the course of the reduction.

Racemic narwedine, and derivatives thereof, can be prepared as outlined in British Patent Application No. 9519267.0. However, a further preferred feature of the first embodiment of the present invention is to carry out the asymmetric reduction on a product resulting from a phenolic coupling reaction, which is likely to be more accessible synthetically than narwedine itself. By this means, all the material can be converted into the required enantiomer at an early stage in the process, resulting in a shorter overall synthesis as shown in Scheme 3, below.

In a second embodiment of the present invention, the enone starting material is already enantio-enriched, and can be in the form of a substantially single enantiomer. The enantio-enriched starting material can be obtained using the process outlined by Barton and Kirby; see above.

In this embodiment, the diastereofacial reactivity of both the substrate and the reducing agent are exploited, a phenomena that has been termed double diastereo-differentiation. Thus, if the correct enantiomer of a reducing agent is chosen for a particular substrate the synergy of their effects produces very high diastereoselectivity. The incorrect choice of reducing agent will lead to much lower selectivity (the concept of "matched" and "mismatched" pairs). It has been found that when (−)-narwedine is reduced with a reagent of complimentary chirality the (−)-galanthamine so formed is substantially free of epigalanthamine (the matched pair). However, when (+)-narwedine is reduced with the same reagent the product is a 1:1 mixture of galanthamine and epigalanthamine (the mismatched pair).

It has been discovered that by employing a process according to the second embodiment of the invention, galanthamine can be prepared in higher enantiomeric excess than the narwedine starting material. Consequently, the process of the invention may be usefully employed after a conventional entrainment process, eg. as described by Barton and Kirby.

The process according to the second embodiment can be carried out after phenolic coupling followed by resolution, which gives the requisite substrate for the reduction.

The reducing agent used in either embodiment is necessarily in enantio-enriched, or substantially single enantiomer, form. Suitable reducing agents include complexes of aluminium hydrides, sodium borohydrides, borane reagents or hydrogenation catalysts with chiral modifiers; chiral hydride reagents eg. (R) or (S) alpine hydride; chiral borane reagents; and chiral hydrogenation catalysts. Examples of suitable chiral modifiers include chiral amino alcohols, such as N-methylephedrine. Preferred reducing agents are those that are not only enantiospecific, with regard to converting essentially only one of two enantiomers, but also diastereoselective in providing the required diastereomer of the target allylic alcohol. A particularly preferred reducing agent is lithium aluminium hydride pre-modified by N-methylephedrine and N-ethyl-2-aminopyridine.

While the reaction taking place in the process of the invention has been classed as a reduction reaction, naturally it embraces hydrogenation reactions also.

The invention is now illustrated by way of the following Examples. Examples 1 and 2 involve reduction of racemic narwedine or a derivative thereof, and Examples 3 and 4 involve reduction of enantiomeric narwedine.

EXAMPLE 1

Preparation of (−)-(4α, 6β)4a,5,9,10,11,12-Hexahydro-3-methoxy-11-methyl-6H-benzofuro[3a,3,2-ef][2]-benzazepin-6-ol (i.e. (−)-Galanthamine)

Lithium aluminium hydride (1M in ether, 1.2 ml, 1.20 mmol) was placed in a two necked round bottom flask fitted with a reflux condenser and nitrogen inlet. (−)-N-methylephedrine (0.23 g, 1.26 mmol) in ether (1 ml) was added dropwise and the solution was heated at reflux for 1 hour then cooled to room temperature. N-Ethyl-2-aminopyridine (0.31 g, 2.52 mmol) in ether (1 ml) was added and the bright yellow solution was heated under reflux for a further 1 hour. The solution was cooled to −78° C. and solid racemic narwedine (0.10 g, 0.35 mmol) was added. The suspension was stirred for 3 hours at −78° C. and then allowed to warm to room temperature over 1 hour. The reaction was quenched with hydrochloric acid (3M, 2 ml). The aqueous layer was removed and basified with KOH to pH 14. The remaining mixture was extracted with dichloromethane (3×10 ml) and the combined organic layers were washed with water (5 ml) and brine (5 ml) and dried over magnesium sulphate. Filtration and evaporation gave an orange oil which was flash chromatographed on silica in dichloromethane-methanol 10:1 to yield (−)-galanthamine (50% e.e.) as a white solid (0.036 g, 36%), pure by NMR.

EXAMPLE 2

(−)-(4α,6β)-4a,5,9,10,11,12-Hexahydro-1-bromo-3-methoxy-11-methyl-6H-benzofuro[3a,3,2-ef][2]-benzazepin-6-ol (i.e. (−)-Bromogalanthamine)

Lithium aluminium hydride (1M in ether, 3.6 ml, 3.6 mmol) was placed in a two necked round bottom flask fitted with a reflux condenser and nitrogen inlet. (−)-N-methylephedrine (0.71 g, 3.95 mmol) in ether (4 ml) was added dropwise and the solution was heated at reflux for 1 hour then cooled to room temperature. N-Ethyl-2-aminopyridine (0.97 g, 2.52 mmol) in ether (5 ml) was added and the bright yellow solution was heated under reflux for a further 1 hour. The solution was cooled to −78° C. and solid racemic bromonarwedine (0.40 g, 1.09 mmol) was added. The suspension was stirred for 3 hours at −78° C. and then allowed to warm to room temperature over 20 hours. The reaction was quenched with hydrochloric acid (2M, 10 ml). The aqueous layer was removed and basified with potassium carbonate to pH 11. The mixture was extracted with dichloromethane (3×10 ml) and the combined organic layers were washed with water (5 ml) and brine (5 ml) and dried over magnesium sulphate. Filtration and evaporation gave an orange oil which was flash chromatographed on silica in dichloromethane-methanol 10:1 to yield (−)-bromogalanthamine (43% e.e.) (53% yield).

EXAMPLE 3 (MATCHED DIASTEREOMERIC REDUCTION)

(−)-(4α,6β)4a,5,9,10,11,12-Hexahydro-3-methoxy-11-methyl-6H benzofuro[3a,3,2-ef][2]-benzazepin-6-ol (i.e. (−)-Galanthamine)

(−)-Narwedine (>98% ee, 0.1 g) was added to a mixture of lithium aluminium hydride (1.2 ml of a 1.0 M solution in ether), (−)-N-methylephedrine (0.23 g) and N-ethyl-2-aminopyridine (0.31 g) in ether at 0° C., and the resulting mixture was stirred at that temperature for 4 h. Sodium hydroxide solution (10 ml of a 1.0 M solution) was added and the product extracted with dichloromethane. Evaporation of the organic phase gave (−)-galanthamine (>98% ee, 85% yield) free of epigalanthamine by GC/MS analysis.

EXAMPLE 4 (MIS-MATCHED REDUCTION)

(+)-(4β,6α-4a,5,9,10,11,12-Hexahydro-3-methoxy-11-methyl-6H-benzofuro[3a,3,2ef][2]-benzazepin-6-ol (i.e. (+)-Galanthamine)

Lithium aluminium hydride (1M in ether, 1.2 ml, 1.20 mmol) was placed in a two necked round bottom flask fitted with a reflux condenser and nitrogen inlet. (−)-N-methyephedrine (0.23 g, 1.26 mmol) in ether (1 ml) was added dropwise and the solution was heated at reflux for 1 hour then cooled to room temperature. N-Ethyl-2-aminopyridine (0.31g, 2.52 mmol) in ether (1 ml) was added and the bright yellow solution was heated under reflux for a further 1 hour. The solution was cooled to −78° C. and solid (+) narwedine (97% e.e) (0.10 g, 0.35 mmol) was added. The suspension was warmed to 0° C., stirred for 20 hours and then allowed to warm to room temperature over 1 hour. The reaction was quenched 2M potassium carbonate (10 ml). The mixture was extracted into ethyl acetate (2×10 ml) and then the combined organic layer was washed with water (5 ml) and brine (5 ml) and dried over magnesium sulphate. Filtration and evaporation gave an orange oil which was shown by NMR and GC-MS to contain galanthamine and epigalanthamine in a 1:1 mixture. Flash chromatography on silica in dichloromethane-methanol 10:1 yielded (+) galanthamine (98% e.e.) (30% yield) and (+)-epigalanthamine (95% e.e) (26% yield).

Scheme 1

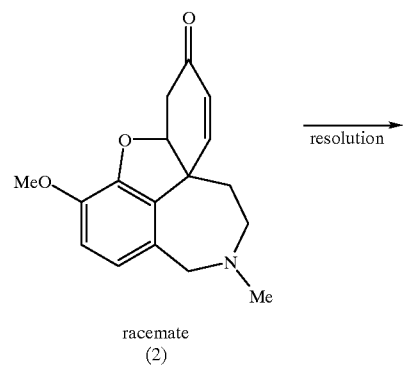

racemate
(2)

-continued
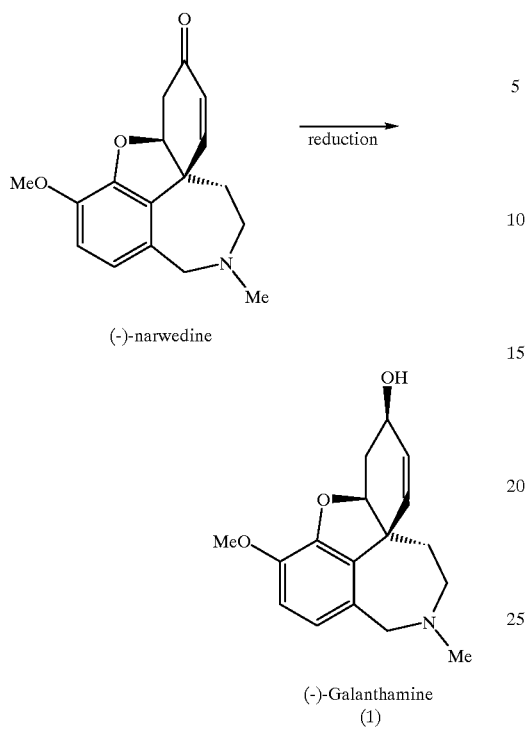
(-)-narwedine
(-)-Galanthamine
(1)
Scheme 2
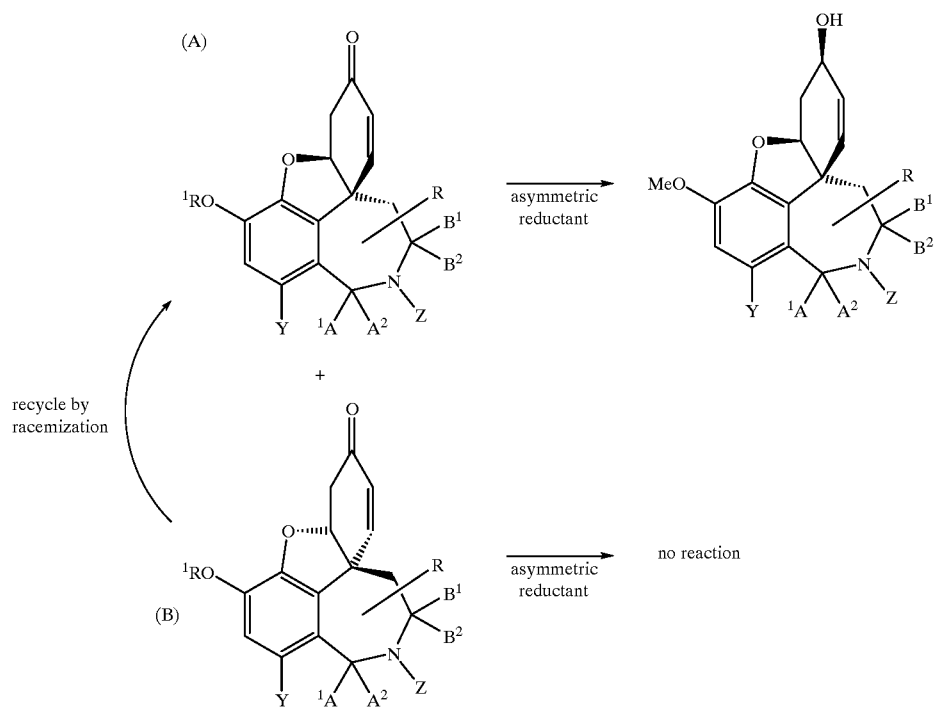

Scheme 3

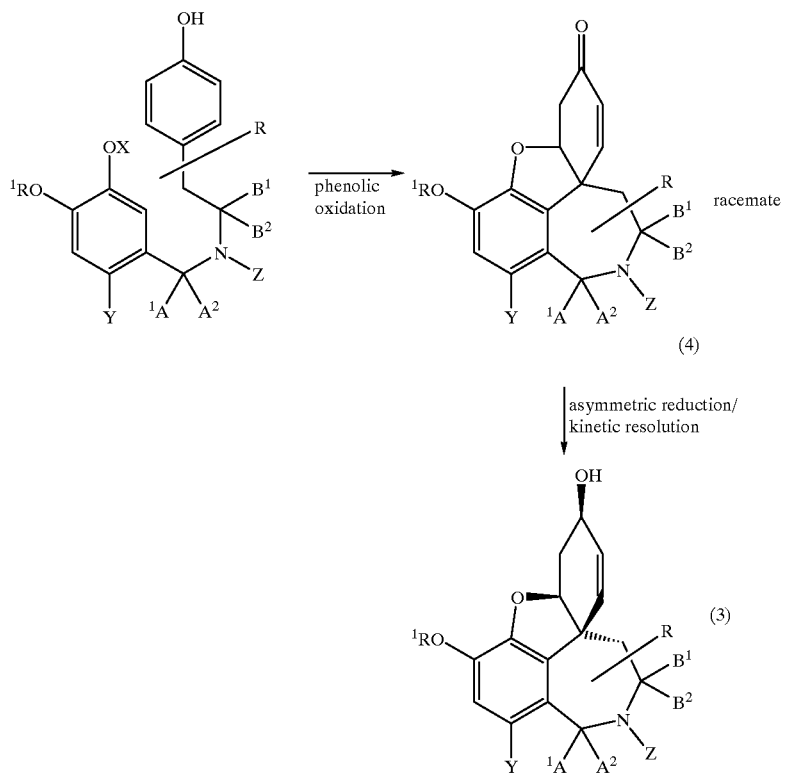

We claim:

1. A process for preparing a compound of formula (3) in enantio-enriched form, the process comprising reducing a compound of formula (4) using an enantio-enriched asymmetric enantiospecific reductant, said reducing agent comprising an archiral reducing agent modified with a chiral additive, wherein $A^1=A^2=H$ or $A^1, A^2=O$; $B^1=B^2=H$ or $B^1, B^2=O$; $Z=H$, a $C_{1-20}$ alkyl group, acyl or alkyloxycarbonyl; $Y=H$, bromo or t-butyl; and $R^1=C_{1-20}$ alkyl.

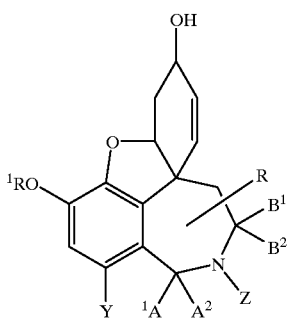
(3)

-continued

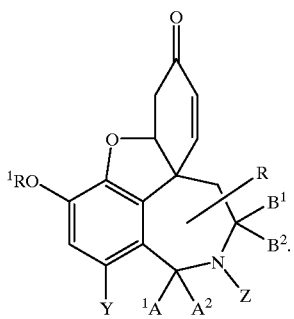
(4)

2. The process according to claim 1, wherein said reducing agent is selected from the group consisting of complexes of aluminum hydrides, sodium borohydrides, borane reagents or hydrogenation catalysts with chiral modifiers; chiral hydride reagents; chiral borane reagents; and chiral hydrogenation catalysts.

3. The process according to claim 2, wherein said reducing agent comprises an aluminum hydride modified with a chiral amino alcohol.

4. The process according to claim 2, wherein said chiral hydride reagents are (R) or (S) alpine hydride.

5. The process according to claim 3, wherein said chiral amino alcohol comprises N-methylephedrine.

6. A compound having the general formula (3)

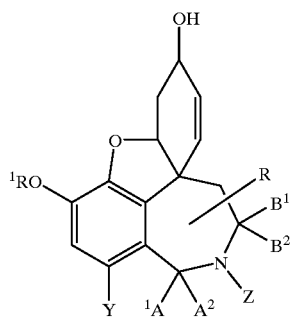

(3)

in substantially single enantiomer form and having a configuration corresponding to (−)-galanthamine, wherein $A^1=A^2=B^1=B^2=H$; $R^1=Me$; Y=H, Bromo, t-butyl, and Z=CHO or a removeable protecting group for nitrogen selected from the group consisting of acyl and alkyloxycarbonyl, provided that the compound is not galanthamine.

7. The compound according to claim 6, which is bromogalanthamine.

* * * * *

UNITED STATES PATENT AND TRADEMARK OFFICE
CERTIFICATE OF CORRECTION

PATENT NO. : 6,018,043
DATED : January 25, 2000
INVENTOR(S) : Ulrich Conrad Dyer, et al.

It is certified that error appears in the above-identified patent and that said Letters Patent is hereby corrected as shown below:

Column 10, line 3: "Bromo" should read --bromo--.

Column 10, line 4: "removeable" should read --removable--.

Column 10, line 6-7: "not galanthamine" should read --not (-)-galanthamine--.

Signed and Sealed this

Twenty-third Day of January, 2001

Attest:

Q. TODD DICKINSON

*Attesting Officer*        *Commissioner of Patents and Trademarks*